United States Patent
Plahey et al.

(10) Patent No.: US 12,059,517 B2
(45) Date of Patent: Aug. 13, 2024

(54) AIR MANAGEMENT IN A CASSETTE OF A DIALYSIS MACHINE

(71) Applicant: Fresenius Medical Care Holdings, Inc., Waltham, MA (US)

(72) Inventors: Kulwinder S. Plahey, Martinez, CA (US); James J. Peterson, Benicia, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1246 days.

(21) Appl. No.: 16/404,809

(22) Filed: May 7, 2019

(65) Prior Publication Data
US 2020/0353144 A1    Nov. 12, 2020

(51) Int. Cl.
*A61M 1/16* (2006.01)
*A61M 1/14* (2006.01)
*A61M 1/28* (2006.01)

(52) U.S. Cl.
CPC ........ *A61M 1/1672* (2014.02); *A61M 1/1522* (2022.05); *A61M 1/1524* (2022.05); *A61M 1/154* (2022.05); *A61M 1/155* (2022.05); *A61M 1/1562* (2022.05); *A61M 1/15632* (2022.05); *A61M 1/1565* (2022.05); *A61M 1/1603* (2014.02); *A61M 1/1623* (2014.02); *A61M 1/166* (2014.02); *A61M 1/287* (2013.01);
(Continued)

(58) Field of Classification Search
CPC ............. A61M 1/1672; A61M 1/1522; A61M 1/1524; A61M 1/154; A61M 1/155; A61M 1/1562; A61M 1/15632; A61M 1/1565; A61M 1/1603; A61M 1/1623; A61M 1/166; A61M 1/287; A61M 1/159; A61M 2205/125; A61M 2205/127; A61M 2205/12; A61M 2205/7536; A61M 1/1658; A61M 1/28
See application file for complete search history.

(56) References Cited

U.S. PATENT DOCUMENTS

| | | |
|---|---|---|
| 4,618,343 A | 10/1986 | Polaschegg |
| 5,421,823 A | 6/1995 | Kamen et al. |
| 5,431,626 A | 7/1995 | Bryant et al. |

(Continued)

FOREIGN PATENT DOCUMENTS

WO    0191829 A2    12/2001

OTHER PUBLICATIONS

International Search Report and Written Opinion for International application No. PCT/US2020/028214, mailed on Jul. 22, 2020, 14 pages.

*Primary Examiner* — Hayden Brewster
(74) *Attorney, Agent, or Firm* — KDW FIRM PLLC (57) ABSTRACT

Dialysis systems and methods for operating dialysis machines (e.g., peritoneal dialysis machines) for conducting dialysis treatments are disclosed. The dialysis system may include a dialysis machine for transferring dialysate to a patient from a dialysate bag. The dialysate may flow from the dialysate bag through a disposable cartridge or cassette positionable within the dialysis machine. A filter may be included in, coupled to, etc., the dialysis machine. In use, the filter may be configured to filter out air content from the dialysate. In some embodiments, the filter may be incorporated into and/or operatively coupled to the disposable cartridge or cassette inserted into the dialysis machine.

19 Claims, 7 Drawing Sheets

(52) U.S. Cl.
CPC ....... *A61M 1/159* (2022.05); *A61M 2205/125* (2013.01); *A61M 2205/127* (2013.01)

(56) References Cited

U.S. PATENT DOCUMENTS

| | | | |
|---|---|---|---|
| 5,591,344 A * | 1/1997 | Kenley | A61M 1/3647 210/764 |
| 5,628,908 A | 5/1997 | Kamen et al. | |
| 7,410,475 B2 | 8/2008 | Krensky et al. | |
| 7,485,260 B2 | 2/2009 | Tamari | |
| 7,731,689 B2 | 6/2010 | Prisco et al. | |
| 7,901,376 B2 | 3/2011 | Steck et al. | |
| 7,988,768 B2 | 8/2011 | Yardimci et al. | |
| 8,025,716 B2 | 9/2011 | Prisco et al. | |
| 8,221,529 B2 | 7/2012 | Childers et al. | |
| 8,287,480 B2 | 10/2012 | Sasaki et al. | |
| 8,425,780 B2 | 4/2013 | Beiriger | |
| 9,555,180 B2 | 1/2017 | Elahi | |
| 9,561,323 B2 | 2/2017 | Plahey et al. | |
| 9,713,665 B2 | 7/2017 | Meyer et al. | |
| 9,775,939 B2 | 10/2017 | Britton et al. | |
| 9,872,949 B2 | 1/2018 | Meyer et al. | |
| 2006/0173395 A1 | 8/2006 | Brugger et al. | |
| 2007/0278155 A1* | 12/2007 | Lo | A61M 1/1639 210/646 |
| 2009/0084721 A1 | 4/2009 | Yardimci et al. | |
| 2009/0088675 A1* | 4/2009 | Kelly | A61M 1/288 604/4.01 |
| 2009/0294359 A1 | 12/2009 | Hopping et al. | |
| 2010/0130918 A1 | 5/2010 | Elahi | |
| 2010/0312172 A1 | 12/2010 | Hoffman | |
| 2010/0312174 A1 | 12/2010 | Hoffman | |
| 2011/0137237 A1 | 6/2011 | Prisco et al. | |
| 2012/0065581 A1* | 3/2012 | Childers | A61M 1/1658 604/29 |
| 2013/0035626 A1 | 2/2013 | Suzuki | |
| 2013/0150768 A1 | 6/2013 | Sakamoto et al. | |
| 2014/0216250 A1* | 8/2014 | Meyer | A61M 1/3627 95/1 |
| 2015/0025449 A1 | 1/2015 | Yuds et al. | |
| 2016/0250405 A1 | 9/2016 | Kogoshi et al. | |
| 2017/0232173 A1* | 8/2017 | Perry | A61M 1/1658 604/29 |
| 2017/0268495 A1 | 9/2017 | Overson et al. | |
| 2017/0296731 A1 | 10/2017 | Crawford et al. | |
| 2019/0076590 A1 | 3/2019 | Plahey et al. | |

\* cited by examiner

AIR MANAGEMENT IN A CASSETTE OF A DIALYSIS MACHINE

FIELD OF THE DISCLOSURE

The disclosure generally relates to dialysis machines, and more particularly to air management in dialysis systems and methods.

BACKGROUND

Dialysis machines are known for use in the treatment of renal disease. The two principal dialysis methods are hemodialysis (HD) and peritoneal dialysis (PD). During HD, the patient's blood is passed through a dialyzer of an HD machine while also passing dialysate through the dialyzer. A semi-permeable membrane in the dialyzer separates the blood from the dialysate within the dialyzer and allows diffusion and osmosis exchanges to take place between the dialysate and the blood stream. During PD, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated PD machines, called PD cyclers, are designed to control the entire PD process so that it can be performed at home, usually overnight, without clinical staff in attendance.

A dialysis machine, such as a PD machine, may include one or more containers (e.g., bags) containing a fluid (e.g., a dialysate) for patient infusion. In PD machines, for example, tubing as fluid lines are inserted into an abdomen of a patient for flowing fresh dialysate and removing used dialysate, waste, and excess fluid. In bags containing fresh dialysate, an amount of air content may also be present, for example, due to fill levels, osmosis, and/or other conditions. If the dialysis machine draws a combination of dialysate and air content (e.g., air bubbles) from one of the bags or elsewhere in the system, the dialysis machine may deliver less than the prescribed volume of dialysate to the patient over the course of the treatment and/or a potentially painful build-up of excess air content in the patient may result. For example, air content delivered to the patient may result in the patient experiencing discomfort, such as shoulder or abdominal pain.

Other events during treatment may occur as well, which may affect the delivery of dialysate. In some embodiments, a dialysis machine may react to these conditions by alerting the patient via an alarm or other notification, and may pause or even stop the treatment. Multiple alarms, particularly alarms during the night, may be a nuisance to the patient. In some embodiments, in order to continue treatment, the dialysis machine may automatically purge the dialysate or combination of dialysate and air content, for example, to a drain. Fresh dialysate that is drained due to air content volume, or another condition, may waste an unacceptable amount of dialysate, and may result in the patient not receiving a full prescribed treatment or a treatment time being unnecessarily extended. When a patient receives less than 90% of a dialysate treatment, it may be considered ineffective. It is further noted that removing air is also an issue during system priming. A large percentage of set-up time a patient experiences before beginning therapy is related to priming. An improved way of removing air from the system during operation could result in shorter priming and set-up time.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a dialysis system for conducting a dialysis treatment is disclosed. The dialysis system comprising a dialysis machine for transferring dialysate to a patient from a dialysate bag, the dialysis machine including a cavity; a disposable cassette positionable within the cavity, the cassette being in fluid communication with the patient and the dialysate bag; and an air chamber including an air vent coupled to the disposable cassette, the air chamber and the air vent being arranged and configured to allow air content to move out of the air chamber through the air vent.

In this and other embodiments, the disposable cassette is arranged and configured so that, in use, air content in the dialysate is directed into the air chamber and through the air vent.

In this and other embodiments, the air chamber is integrally formed with the disposable cassette.

In this and other embodiments, the air chamber is formed in a top portion of the disposable cassette.

In this and other embodiments, the disposable cassette includes one or more sensors and one or more valves, the machine being arranged and configured so that an air content in the dialysate is detectable via the one or more sensors, and when the air content in the dialysate exceeds a target value, the one or more valves are controllable to direct the air content into the air chamber.

In this and other embodiments, the air content is directed out of the air chamber through the air vent.

In this and other embodiments, the air chamber is pressurized to move the air content out of the air chamber.

In this and other embodiments, the dialysis system further comprises an air filter configured to allow air content to move through the air vent.

In this and other embodiments, the air filter is a hydrophobic filter.

In this and other embodiments, the air chamber is regulated so that pressure moves the air content out of the air chamber and through the air filter and air vent until a spike in pressure is detected.

In this and other embodiments, the air chamber is formed in a separate housing, the air chamber being in fluid communication with the disposable cassette.

In this and other embodiments, the air chamber is coupled to the disposable cassette via a membrane.

In this and other embodiments, the air chamber is coupled to the disposable cassette via a one-way valve.

In this and other embodiments, the air content is moved from the disposable cassette into the air chamber via a positive pressure from the disposable cassette, a negative pressure from the air chamber, or a pump, or combinations thereof.

In this and other embodiments, the air content is moved from the disposable cassette into the air chamber via a positive pressure from the disposable cassette, a negative pressure from the air chamber, or a pump, or combinations thereof.

In this and other embodiments, the dialysis system further comprises an air filter configured to allow air content to move through the air vent.

According to an exemplary embodiment of the present disclosure, a method for conducting a dialysis treatment is disclosed. The method comprising inserting a disposable cassette into a dialysis machine; transferring dialysate to a patient from a dialysate bag via tubing, the dialysate traveling through the disposable cassette; and filtering out air content from the dialysate by a filter coupled to the disposable cassette.

In this and other embodiments, the method further comprises cleaning the filter by intermittently delivering fresh dialysate to the filter.

In this and other embodiments, the air content is filtered out from the dialysate before entering the disposable cassette, after exiting the disposable cassette, or both.

In this and other embodiments, the dialysate from the dialysate bag is flowed through a warmer pouch before traveling through the disposable cassette.

According to an exemplary embodiment of the present disclosure, a disposable cassette positionable within a cavity of a dialysis machine is disclosed. The cassette being in fluid communication with a patient and a dialysate bag for transferring dialysate therebetween. The disposable cassette comprising an air chamber including an air vent, the air chamber and the air vent being arranged and configured to allow air content to move out of the air chamber through the air vent.

In this and other embodiments, the disposable cassette further comprises one or more sensors for detecting air content in the dialysate; and one or more valves for directing the air content into the air chamber when the air content in the dialysate exceeds a target value.

In this and other embodiments, the air chamber is integrally formed with the disposable cassette.

In this and other embodiments, the air chamber is formed in a top portion of the disposable cassette.

In this and other embodiments, the air content is directed out of the air chamber through the air vent.

In this and other embodiments, the air chamber is pressurized to move the air content out of the air chamber.

In this and other embodiments, the disposable cassette further comprises an air filter configured to allow air content to move through the air vent.

In this and other embodiments, the air chamber is regulated so that pressure moves the air content out of the air chamber and through the air filter and air vent until a spike in pressure is detected.

In this and other embodiments, the air chamber is formed in a separate housing, the air chamber being in fluid communication with the disposable cassette.

In this and other embodiments, the air chamber is coupled to the disposable cassette via a membrane or a one-way valve.

In this and other embodiments, the air content is moved into the air chamber via a positive pressure from the disposable cassette, a negative pressure from the air chamber, or a pump, or combinations thereof.

BRIEF DESCRIPTION OF THE DRAWINGS

By way of example, specific embodiments of the disclosed methods and devices will now be described, with reference to the accompanying drawings, in which.

DETAILED DESCRIPTION

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of dialysis machines and of methods for operating dialysis machines may minimize potential dialysate waste, e.g., so a patient may receive a fuller prescribed treatment, treatment times may be efficient, and use of valuable treatment resources may be conserved and optimized to the benefit of the patient, hospital, dialysis centers, environment, etc. As described above, each fluid bag may contain a quantity of air content, which may be present as a result of the bag being not completely filled with fluid during manufacture. Additionally, fluid bags may be stored for a period of time prior to sale and/or use by a patient, e.g., 1-2 years or longer. Certain bag materials may be more susceptible to osmosis, for example, a Biofine™ material bag may have a greater amount of air content after a period of storage than a bag made of a different material, such as a polyvinyl chloride (PVC) material. For example, a bag may contain a range of approximately 20 cc to 150 cc of air content. Although the term "bag" is used throughout, it should be understood that a fluid bag may be any type of container capable of holding a fluid, e.g., a dialysate. In some embodiments, a fluid container may include a container in which dry concentrates are mixed with water to generate dialysate suitable for a dialysis treatment.

To ensure patients safely and efficiently receive the proper amount of dialysis treatment, air content in a dialysis machine may be minimized by sensor detection and alarms. When a predetermined volume of air content is detected in the dialysate during treatment, the dialysis machine may be configured to purge or drain waste instead of flowing the dialysate into a patient.

When air content is present in the dialysate or system, or another treatment event condition occurs where it is necessary for flow to the patient to be temporarily paused, the dialysate may be unusable for flowing into a patient. When unusable dialysate is dumped via a drain, dialysate that was prescribed to the patient is wasted. Each event of unusable dialysate may result in a range of approximately 30 mL to 100 mL of dialysate being drained instead of flowing into a patient. As one to several events may occur in a single treatment, this wasted dialysate may result in a patient not receiving as full a prescribed treatment as might be possible, and treatment time and use of resources may not be optimal.

It may therefore be advantageous as described herein to improve dialysate flow management to minimize dialysate purging when air content is present by including a device as part of a dialysis machine, which removes the air content from the machine or otherwise allows the air content to escape from the machine, e.g., through a filter, without any, or minimizing to a much less extent, draining or purging solution that would otherwise be usable.

According to an aspect of the system described herein, and as further detailed below, an air management device may be added to the cassette to provide for removal of air content during operation of a dialysis machine, such as a PD cycler. In an embodiment, the air management device may include an air chamber and vent integrated with and/or otherwise coupled to the cassette of the PD cycler.

Figure 1:
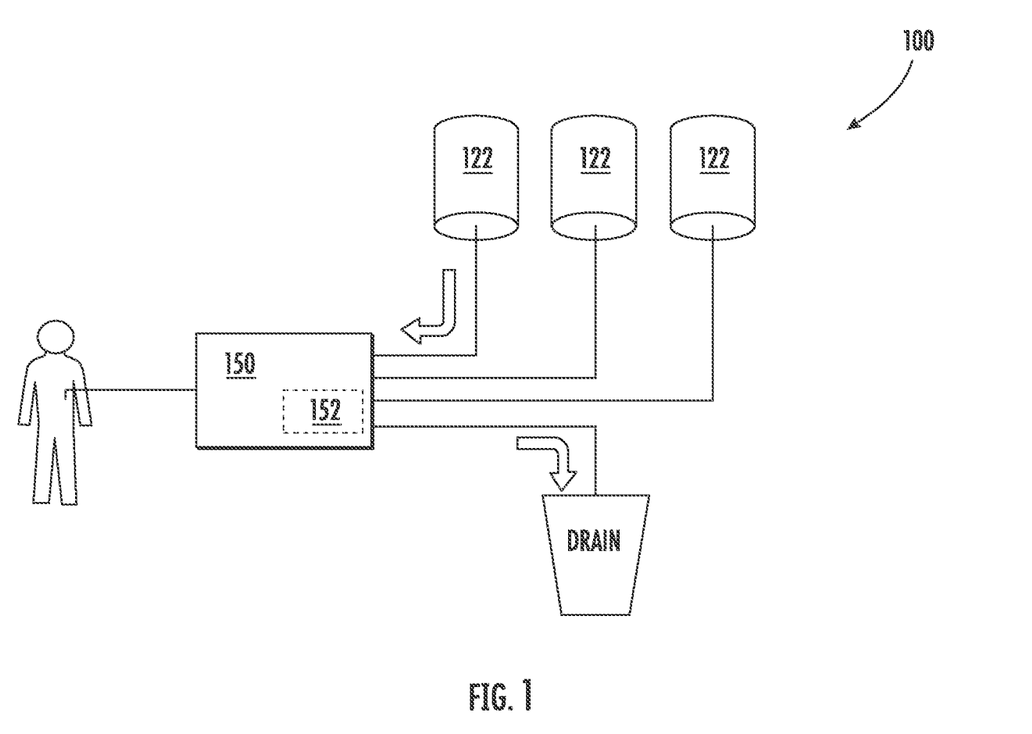
FIG. 1 illustrates an example of an embodiment of a dialysis system in accordance with an aspect of the present disclosure.

Referring to FIG. 1, a dialysis system 100 may include a PD machine 150, for flowing fresh dialysate into a patient and draining used dialysate out of the patient. During treatment, a volume of dialysate may enter the patient's abdomen and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the used dialysate may be flowed out of the patient's abdomen and purged to a drain connected to the tubing, e.g., the drain line. This exchange of fresh dialysate and used dialysate after a dwell time may occur for several cycles depending on the patient's treatment regimen.

Dialysate bags 122 may be connected to the dialysis machine 150. In some embodiments, hanging the dialysate bags 122 may improve air content management as any air content is disposed by gravity to a top portion of the dialysate bag 122. Valves may be attached to a bottom portion of the dialysate bags 122 so fluid is drawn out and air content delivery is minimized. In one embodiment, as shown, dialysate from the dialysate bags 122 may be transferred directly to the patient through a warmer pouch, a heater bag, or the like 152 (used interchangeably herein without the intent to limit). When the dialysate has reached a predetermined temperature (e.g., approximately 98°-100° F., 37° C.) in the warmer pouch 152, the dialysate may be flowed into the patient. The dialysate bags 122 and/or the warmer pouch 152 may be connected to a cartridge or cassette (used interchangeably without the intent to limit), which may be insertable into the dialysis machine 150, via dialysate bag lines and/or warmer pouch line, and the dialysate bag lines may be used to pass dialysate from dialysate bags 122 to the cassette during use. In use, the cassette may be disposable. Alternatively, the cassette may be reusable. In addition, a patient line and a drain line may be connected to the cassette. The patient line may be connected to a patient's abdomen via a catheter and may be used to pass dialysate back and forth between the cassette and the patient's peritoneal cavity during use. The drain line may be connected to a drain or drain receptacle and may be used to pass dialysate from the cassette to the drain or drain receptacle during use.

Figure 2:
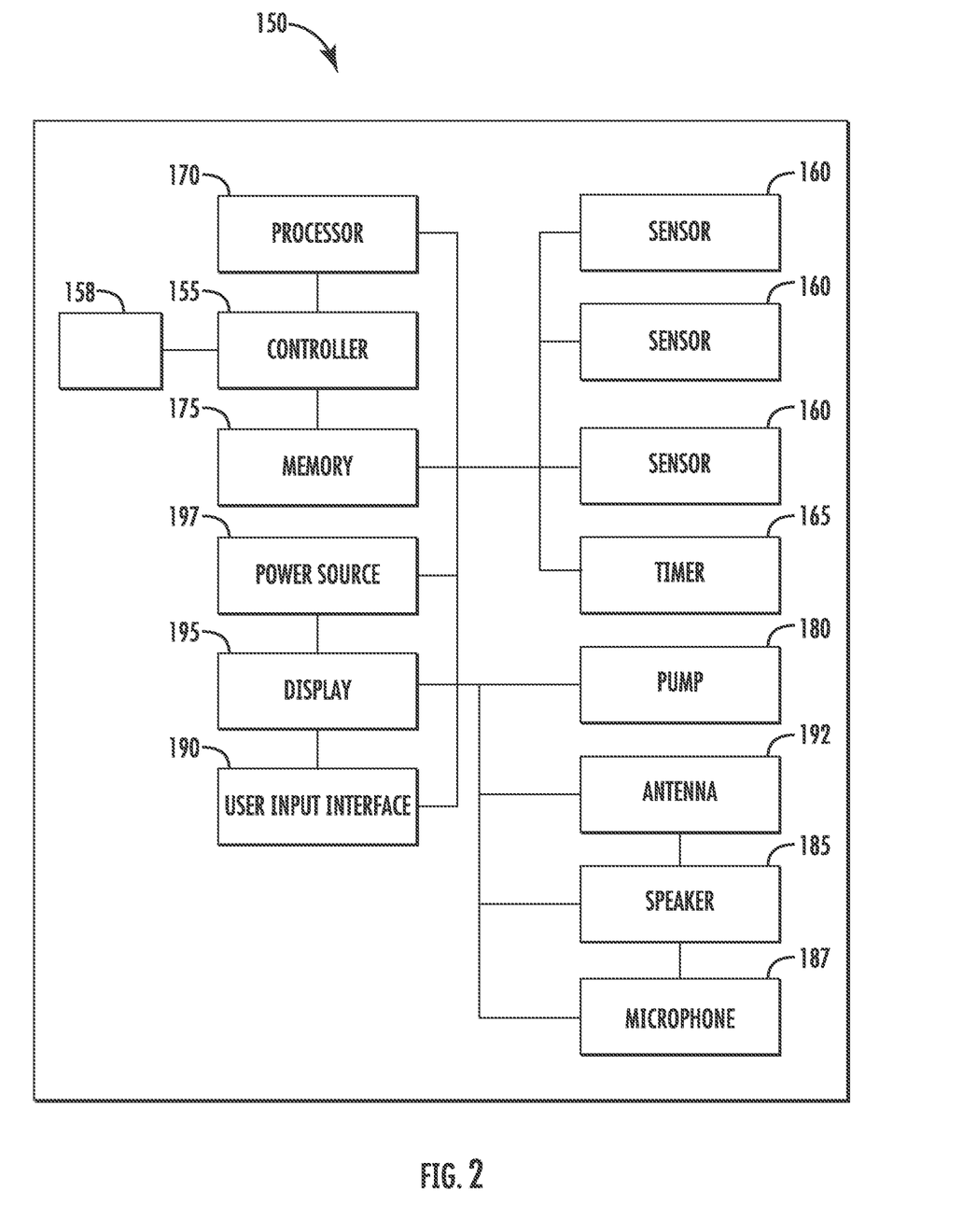
FIG. 2 is a block diagram illustrating an example of an embodiment of a dialysis machine and a controller in accordance with an aspect of the present disclosure.

Referring to FIG. 2, a schematic of an exemplary embodiment of a dialysis machine such as, for example, dialysis machine 150 and a controller 155 in accordance with the present disclosure are shown. The machine 150 may be a home dialysis machine, e.g., a PD machine, for performing a dialysis treatment on a patient, and may be included in the system 100 described above with respect to FIG. 1. The controller 155 may automatically control execution of a treatment function during a course of dialysis treatment. The controller 155 may be operatively connected to the sensors 160 and deliver a signal to execute a treatment function (e.g., transferring dialysate from the dialysate bag 122 through the warmer pouch 152 and then to the patient), or a course of treatment associated with various treatment systems. In some embodiments, a timer 165 may be included for timing triggering of the sensors 160.

In some embodiments, the machine 150 may also include a processor 170, and memory 175, the controller 155, the processor 170, and/or the memory 175, or combinations thereof of the machine 150, may receive signals from the sensor(s) 160 indicating, for example, a dialysate air content. Each fluid bag (e.g., the dialysate bags 122) may contain an approximate amount of dialysate, such that "approximate amount" may be defined as a 3 L fluid bag containing 3000 to 3150 mL, a 5 L fluid bag containing 5000 to 5250 mL, and a 6 L fluid bag containing 6000 to 6300 mL. The controller 155 may also detect connection of all fluid bags 122 connected. As described above, each fluid bag 122 may contain some amount of air content, which may change over time.

Communication between the controller 155 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In some embodiments, the dialysis machine 150 may include at least one pump 180 operatively connected to the controller 155. During a treatment operation, the controller 155 may control the pump 180 for pumping fluid, e.g., fresh and spent dialysate, to and from a patient. The pump 180 may also pump dialysate from the dialysate bag 122 through, for example, the warmer pouch 152. The controller 155 may also be operatively connected to a speaker 185 and a microphone 187 disposed in the machine 150. A user input interface 190 may include a combination of hardware and software components that allow the controller 155 to communicate with an external entity, such as a patient or other user. These components may be configured to receive information from actions such as physical movement or gestures and verbal intonation. In some embodiments, the components of the user input interface 190 may provide information to external entities. Examples of the components that may be employed within the user input interface 190 include keypads, buttons, microphones, touch screens, gesture recognition devices, display screens, and speakers. The machine 150 may also be wirelessly connectable via an antenna 192 for remote communication. The machine 150 may also include a display 195 and a power source 197.

As shown in FIG. 2, the sensors 160 may be included for monitoring parameters and may be operatively connected to at least the controller 155, the processor 170, and/or the memory 175, or combinations thereof. The processor 170 may be configured to execute an operating system, which may provide platform services to application software, e.g., for operating the dialysis machine 150. These platform services may include inter-process and network communication, file system management and standard database manipulation. One or more of many operating systems may be used, and examples are not limited to any particular operating system or operating system characteristic. In some examples, the processor 170 may be configured to execute a real-time operating system (RTOS), such as RTLinux, or a non-real time operating system, such as BSD or GNU/Linux.

According to a variety of examples, the processor 170 may be a commercially available processor such as a processor manufactured by INTEL, AMD, MOTOROLA, and FREESCALE. However, the processor 170 may be any type of processor, multiprocessor or controller, whether commercially available or specially manufactured. For instance, according to one example, the processor 170 may include an MPC823 microprocessor manufactured by MOTOROLA.

The memory 175 may include a computer readable and writeable nonvolatile data storage medium configured to store non-transitory instructions and data. In addition, the memory 175 may include a processor memory that stores data during operation of the processor 170. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 175 may include executable programs or other code that may be executed by the processor 170. The instructions may be persistently stored as encoded signals, and the instructions may cause the processor 170 to perform the functions described herein. The memory 175 may include information that is recorded, on or in, the medium, and this information may be processed by the processor 170 during execution of instructions. The memory 175 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 155.

The sensor(s) 160 may include a pressure sensor for monitoring fluid pressure of the machine 150, although the sensors 160 may also include any of a heart rate sensor, a respiration sensor, a temperature sensor, a weight sensor, an air sensor, a video sensor, a thermal imaging sensor, an electroencephalogram sensor, a motion sensor, an audio sensor, an accelerometer, a capacitance sensor, or any other suitable sensor. It is appreciated that the sensors 160 may include sensors with varying sampling rates, including wireless sensors.

The controller 155 may be disposed in the machine 150 or may be coupled to the machine 150 via a communication port or wireless communication links, shown schematically as communication element 158. According to various examples, the communication element 158 may support a variety of one or more standards and protocols, examples of which include USB, WiFi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 150, the controller 155 may be operatively connected to any of the sensors 160, the pump 180, and the like. The controller 155 may communicate control signals or triggering voltages to the components of the machine 150. As discussed, exemplary embodiments of the controller 155 may include wireless communication interfaces. The controller 155 may detect remote devices to determine if any remote sensors are available to augment any sensor data being used to evaluate the patient.

Figure 3A:
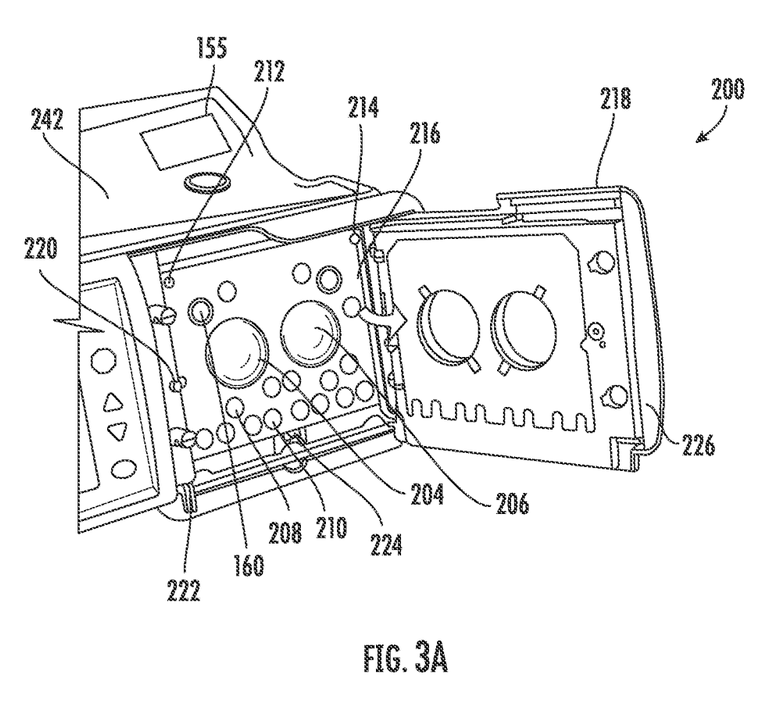
FIGS. 3A-3C illustrate an example of an embodiment of a dialysis machine in accordance with an aspect of the present disclosure.
Figure 3B:
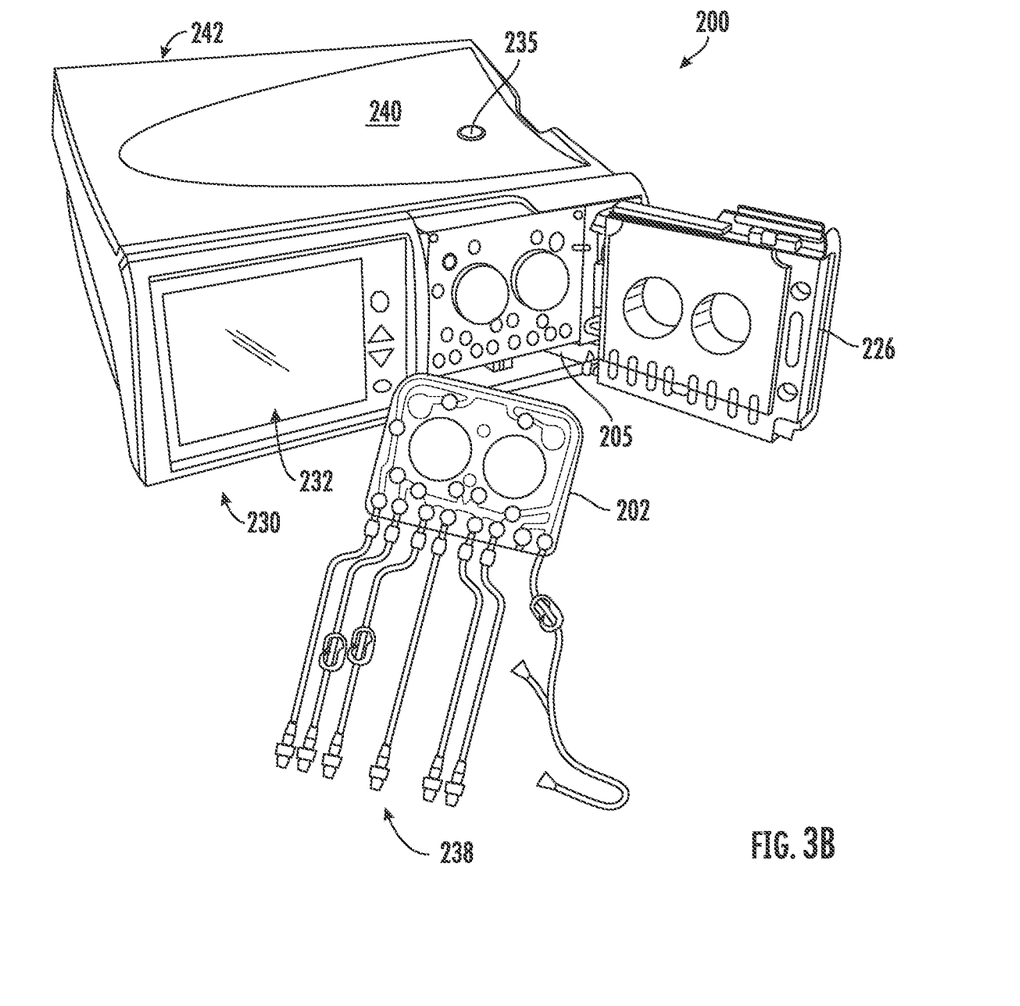
Figure 3C:
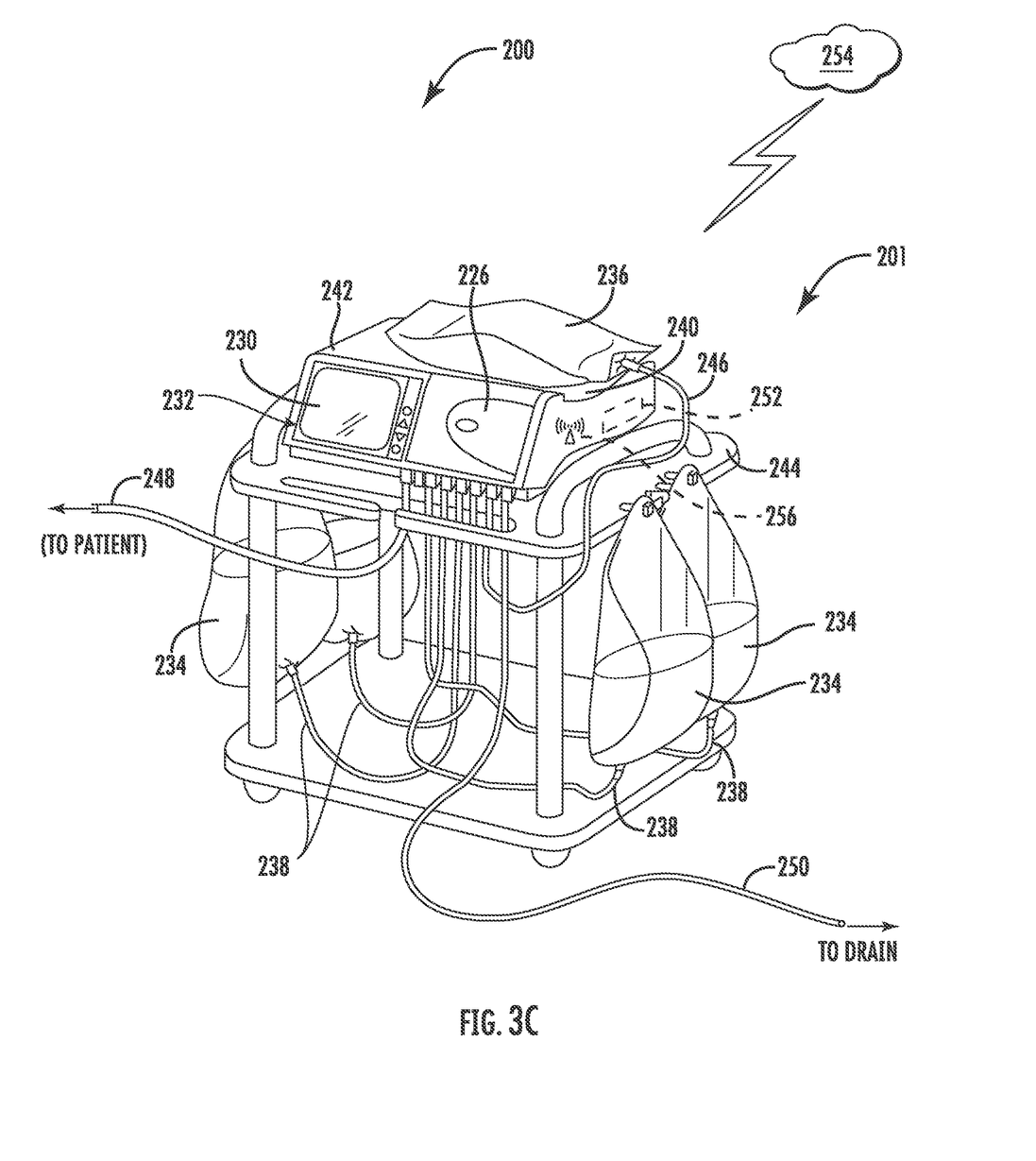

Referring now to FIGS. 3A-3C, an example of an embodiment of a dialysis machine 200 and dialysis system 201 in accordance with the present disclosure is shown. The dialysis system 201 and the machine 200 may include the components described above with respect to the schematic of the system 100 and the machine 150 illustrated in FIGS. 1 and 2. The machine 200 may be configured to provide home dialysis treatment, for example, PD. In some implementations, the system 201 may be a home PD system, e.g., a PD system configured for use at a patient's home. The dialysis system 201 may include the dialysis machine 200 and in some embodiments the machine may be positionable on a cart 244.

The machine 200 may include a housing 242, a door 226, and a cassette interface including pump heads 204, 206 for contacting a disposable cartridge or cassette 202 (used interchangeably without the intent to limit), where the cassette 202 is located within a compartment formed between the cassette interface and the closed door 226 (e.g., cavity 205). Fluid lines (e.g., tubing) may be coupled to the cassette 202 in a known manner, such as via a connector, and may further include valves for controlling fluid flow to and from fluid bags including fresh dialysate and warming pouch. In some embodiments, when a cassette 202 is incorporated, at least a portion of the fluid lines (e.g., tubing) may be integral to the cassette 202. Prior to operation, a user may open the door 226 to insert a fresh cassette 202, and to remove the used cassette 202 after operation.

The cassette 202 may be placed in the cavity 205 of the machine 200 for operation. The machine 200 may manage flowing dialysate into a patient's abdomen, and removal of the used dialysate and waste after a predetermined amount of time. During operation, dialysate fluid may be flowed into a patient's abdomen via the cassette 202, and spent dialysate, waste, and/or excess fluid may be removed from the patient's abdomen via the cassette 202. In some embodiments, cassette guide pins 212, 214 may be present to ensure proper alignment of the cassette 202 when inserted into the machine 200. A cassette pump plate 216 may be provided, which may contain a pump mechanism and provide openings for the pump heads to operate on an inserted cassette 202. The machine 200 may also include a door latch 218, a door sensor 220, a safety clamp 222, and a cassette catch 224, which, in use, may be configured to ensure proper alignment and engagement with a cassette 202 once inserted and once the cassette door 226 is closed.

While the dialysate is present in a peritoneal cavity of the patient, the dialysate may absorb contaminants and/or particulates from the patient's blood. PD uses the patient's peritoneum in the abdomen as a membrane across which fluids and dissolved substances (e.g., electrolytes, urea, glucose, albumin, osmotically active particles, and other small molecules) are exchanged from the blood. PD for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

The machine 200 may include a pressure sensor 160 for providing readings on the fluid (e.g., dialysate). As discussed above, pressure readings may be taken at various intervals during a dialysis operation to provide fluctuation data from which to extrapolate, for example, a patient heart rate and/or a patient respiration rate. In some embodiments, additional instruments or sensors may be employed to provide direct measurement of heart rate, respiration rate, and/or other biological characteristics pertinent to determining a sleep state.

The machine 200 may operate the pump heads 204, 206 to move the fluid. The pump heads 204, 206 apply force to the cassette 202, that connect a fluid reservoir, e.g., dialysate bags 234 to a catheter at the patient's peritoneum. By operation of the pump heads 204, 206, fresh dialysate may be introduced into the patient's peritoneum. Likewise, the pump heads 204, 206 may draw fluid from the patient's peritoneum into a fluid reservoir. Multiple dialysate bags 234 may be used including a clean fluid reservoir and a waste fluid reservoir. Operation of the pump heads 204, 206 in conjunction with valves such as, for example, valves 208, 210, controls delivery or retrieval of fluid.

The machine 200 may also include a heater tray 240. As shown in FIG. 3B, the heater tray 240 may be positioned on top of the housing 242. The heater tray 240 may be any size and shape to accommodate a bag of dialysate (e.g., a 5 L bag of dialysate) for batch heating. The dialysis machine 200 may also include a user interface such as a touch screen 232 and a control panel 230 operable by a user (e.g., a caregiver or a patient) to allow, for example, set up, initiation, and/or termination of a dialysis treatment. In some embodiments, the heater tray 240 may include a heating element 235, for heating the dialysate prior to delivery into the patient.

Dialysate bags 234 may be suspended from hooks on the sides of the cart 244, and a heater bag 236 may be positioned in the heater tray 240. Hanging the dialysate bags 234 may improve air management as air content may be disposed by gravity to a top portion of the dialysate bag 234. Although four dialysate bags 234 are illustrated in FIG. 3C, any number "n" of dialysate bags may be connectable to the dialysis machine 200 (e.g., 1 to 5 bags, or more), and reference made to first and second bags is not limiting to the total number of bags used in a dialysis system 201. For example, the dialysis machine may have dialysate bags 234a, . . . 234n connectable in the system 201. In some embodiments, connectors and tubing ports may connect the dialysate bags 234 and lines for transferring dialysate. Dialysate from the dialysate bags 234 may be transferred to the heater bag 236 in batches. For example, a batch of dialysate may be transferred from the dialysate bags 234 to the heater bag 236, where the dialysate is heated by the heating element 235. When the batch of dialysate has reached a predetermined temperature (e.g., approximately 98°-100° F., 37° C.), the batch of dialysate may be flowed into the patient. The dialysate bags 234 and the heater bag 236 may be connected to the cassette 202 via dialysate bag lines or tubing 238 and a heater bag line or tubing 238, respectively. The dialysate bag lines 238 may be used to pass dialysate from dialysate bags 234 to the cassette 202 during use, and a heater bag line 246 may be used to pass dialysate back and forth between the cassette 202 and the heater bag 236 during use. In addition, a patient line 248 and a drain line 250 may be connected to the cassette 202. The patient line 248 may be connected to a patient's abdomen via a catheter and may be used to pass dialysate back and forth between the cassette 202 and the patient's peritoneal cavity by the pump heads 204, 206 during use. The drain line 250 may be connected to a drain or drain receptacle and may be used to pass dialysate from the cassette 202 to the drain or drain receptacle during use.

The touch screen 232 and the control panel 230 may allow an operator to input various treatment parameters to the dialysis machine 200 and to otherwise control the dialysis machine 200. In addition, the touch screen 232 may serve as a display. The touch screen 232 may function to provide information to the patient and/or the operator of the dialysis system 201. For example, the touch screen 232 may display information related to a dialysis treatment to be applied to the patient, including information related to a prescription.

The dialysis machine 200 may also include a processing module 252 that resides inside the dialysis machine 200, the processing module 252 being configured to communicate with the touch screen 232 and the control panel 230. The processing module 252 may be configured to receive data from the touch screen 232, the control panel 230, sensors such as, for example, weight, air content, flow, temperature, and/or pressure sensors, and control the dialysis machine 200 based on the received data. For example, the processing module 252 may adjust the operating parameters of the dialysis machine 200.

The dialysis machine 200 may also be configured to connect to a network 254. The connection to network 254 may be via a wired and/or wireless connection. The dialysis machine 200 may include a connection component 256 configured to facilitate the connection to the network 254. The connection component 256 may be a transceiver for wireless connections and/or other signal processor for processing signals transmitted and received over a wired connection. Other medical devices (e.g., other dialysis machines) or components may be configured to connect to the network 254 and communicate with the dialysis machine 200.

The user interface portion such as the touch screen and/or display 232 may include one or more buttons for selecting and/or entering user information. The touch screen and/or display 232 may be operatively connected to a controller (not shown) and disposed in the machine 200 for receiving and processing the inputs to operate the dialysis machine 200.

As previously described in connection with the machine 150, the dialysis machine 200 may also include a controller such as, for example, controller 155. The controller for dialysis may be substantially similar in structure and function to controller 155, thus for sake of brevity the entire description of the controller is not repeated here. In use, the controller 155 may be disposed in the machine 200 or may be coupled to the machine 200, or other external systems, via a communication port or wireless communication links. As previously discussed, as a component disposed within the machine 200, the controller 155 may be operatively connected to any one or more of the sensors, pump, pump heads 204, 206, and the like. The controller 155 may communicate control signals or triggering voltages to the components of the machine 200, and may include wireless communication interfaces. The controller 155 may detect remote devices to determine if any remote sensors are available to augment any sensor data being used to evaluate the patient. For example, remote devices may include smart phone microphones, video cameras, cameras, thermal imaging cameras, in bed sensors, sleep manager applications and sensors, web cameras, fitness sensors, stand-alone sensors, and the like.

Figure 4:
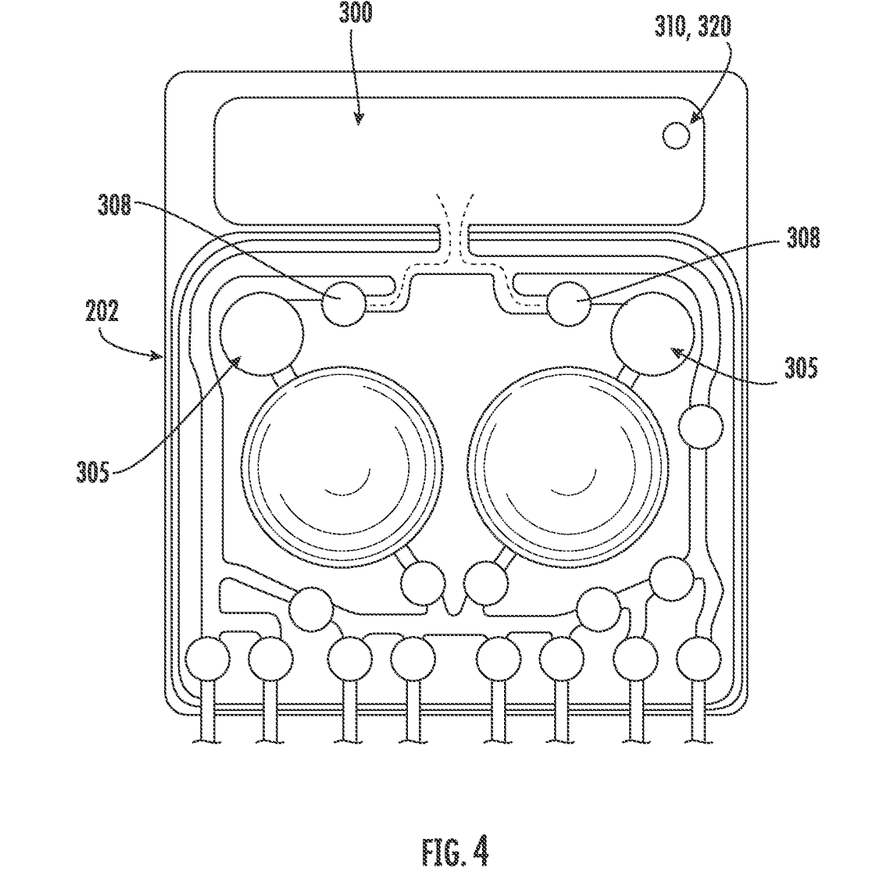
FIG. 4 illustrates an example of an embodiment of a cartridge or cassette in accordance with an aspect of the present disclosure, which can be used in connection with the dialysis machine shown in FIGS. 3A-3C, the cartridge or cassette including an air chamber in accordance with an aspect of the present disclosure.

Referring to FIG. 4, in accordance with one aspect of the present disclosure, the cassette such as, for example, cassette 202, may also include an air chamber 300 and an air vent 310. In use, the air chamber 300 and an air vent 310 may facilitate filtering out air content from a liquid such as dialysate.

As previously mentioned, the machine 200 may include a cavity 205 positioned between a door 226 and a cassette interface including pump heads 204, 206 for receiving and contacting the disposable cassette 202. That is, in use, the cassette 202 is located within a compartment or cavity 205 formed between the cassette interface and the closed door 226. Thus arranged, the orientation of the cassette 202 within the machine 200 is known. As such, the cassette 202 may be arranged and configured so that, in use, air content in the liquid can be directed into the air chamber 300 and through the air vent 310. For example, the cassette 202 may be formed with an air chamber 300 in the top portion thereof. By forming the air chamber 300 in the top portion of the cassette 202, air content management may be improved as any air content is disposed by gravity to a top portion of the liquid. It is noted that the system described herein may be used in connection with other orientations and configurations of a cassette in a dialysis machine, in which the configuration and/or orientation of the cassette is predetermined, and for which the positioning of the air chamber 300 and air vent 310 may be appropriately adjusted to provide air management functionality with the predetermined cassette configuration and/or orientation.

The cassette 202 may include one or more sensors, such as, for example, pressure sensors 305. In addition, the cassette 202 may include one or more valves 308. In use, as previously mentioned, the machine 200, utilizing sensors, may detect, determine, etc., the air content in the dialysate. When air content is detected in the dialysate, the air content may be directed, via manipulation of the valves, into the air chamber 300 rather than to the drain. Once in the air chamber 300, the air content can be directed out of the cassette 202 through the air vent 310. For example, in one embodiment, utilizing pumps, valves and/or sensors, the air chamber 300 can be pressurized to move, push, etc., air content out of the air vent 310 of air chamber 300 formed in the cassette 202.

In one embodiment, the air vent 310 may include a filter 320. The filter 320 may be any suitable filter such as, for example, a hydrophobic filter, so that the air content may flow through the filter 320, but liquid such as the dialysate may be prevented by the filter 320 from exiting the cassette 202. That is, for example, in one embodiment, the filter 320 may include a plurality of pores sized and configured to allow air content to flow through the filter 320 but prevent liquid from flowing through the filter 320. One example of an embodiment of a filter that may be used is disclosed in U.S. Published Patent Application No. 2019/0076590 A1 to Plahey et al., entitled "Hydrophobic Filters for Air Management in Dialysis Machines," which is incorporated herein by reference. The filter 320 may be formed as a flexible material, and may be formed in any suitable shape.

In one embodiment, air content within the air chamber 300 may flow through the air vent 310. Alternatively, in another embodiment, the pressure may be monitored by, for example, one or more of the sensors (e.g., pressure sensors). Thus arranged, the pressure can be regulated so that enough pressure exists to facilitate moving the air content out of the air chamber 300 and through the air vent 310 but controlled within the limits of the filter 320. That is, by knowing the pressure limits of the filter 320, the air content can be moved out of the air chamber 300 by pushing the air content in the air chamber 300 until a spike in pressure is detected, which indicates that all of the air content has been removed from the air chamber 300/cassette 202, and that liquid solution is filling the air chamber 300.

Figure 5A:
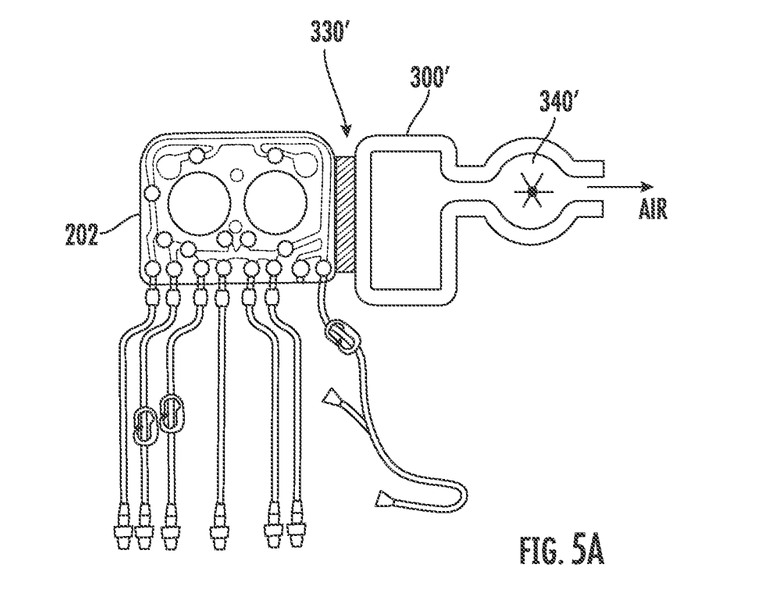
FIGS. 5A and 5B illustrate alternate examples of an air chamber in accordance with an aspect of the present disclosure, which can be used with the cartridge or cassette used in connection with the dialysis machine shown in FIGS. 3A-3C.

It should be appreciated that while the air chamber 300 including the air vent 310 have been described and shown in FIG. 4 as being integrated into the cassette, it is envisioned that the air chamber 300 may be separated from the cassette and coupled thereto. For example, referring to FIGS. 5A and 5B, the air chamber 300' may be provided in a separate housing from the cassette 202. In use, the air chamber 300' may be operatively coupled to the cassette 202 by any suitable mechanism now known or hereafter developed. For example, as illustrated in FIG. 5A, the air chamber 300' may be coupled to the cassette 202 via a membrane 330', such as, for example, a semi-permeable hydrophobic membrane as previously described.

Figure 5B:
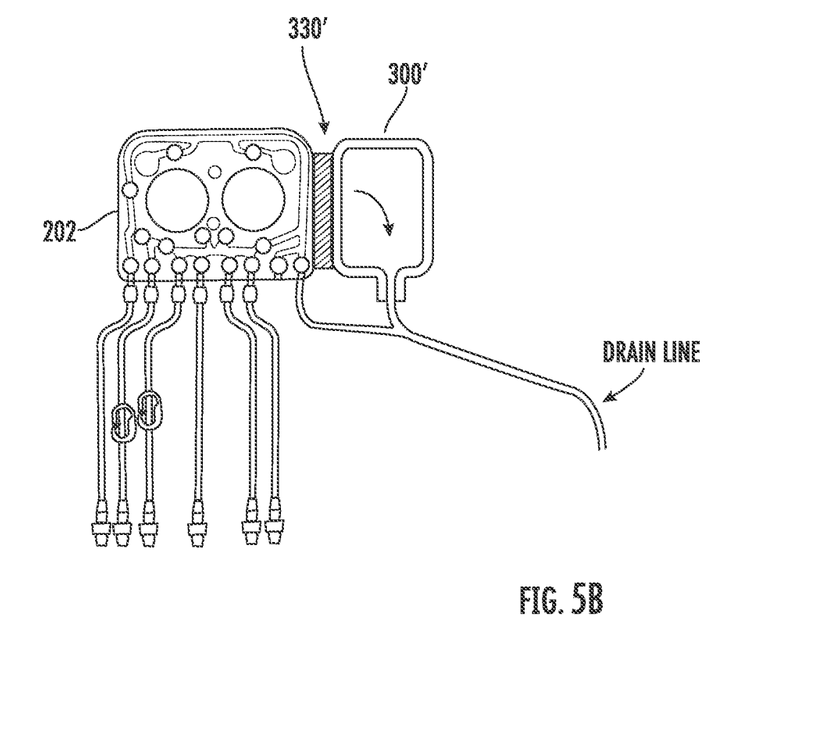

Alternatively, the air chamber 300' may be coupled to the cassette 202 via a valve such as, for example, a one-way valve or the like. In use, air content can be moved, driven, pushed, etc. into the air chamber 300' by any suitable mechanism now known or hereafter developed including, for example, pressure differential such as, for example, positive pressure from the cassette pumps or negative pressure on the chamber side. As shown in FIG. 5A, the negative pressure may be generated by, for example, a pump 340' used to pull the air content from the cassette and into the air chamber 300'. Alternatively, as shown in FIG. 5B, the fluid flow from the drain line may be used to create a siphoning effect, for example, the hydrostatic head pressure could be used to generate a negative pressure in the air chamber 300', which would pull the air content from the cassette into the air chamber 300' and eventually to drain.

As will be appreciated by one of ordinary skill in the art, as with the case with many filters (e.g., hydrophobic filter or membranes) used in medical devices, the filter may become fouled over time. For example, when liquid contacts the filter and the air content evaporates, the resultant biological material containing, for example, salts, sugars, proteins, fats, cells, cellular debris, etc., may collect on the surface of the filter, rendering the filter ineffective or impermeable after a period of time. In accordance with another aspect of the present disclosure, a system and mechanism for cleaning the filter is also disclosed. In connection with providing an air chamber and filter in fluid connectivity with the cassette, the liquid dialysate solution contains only water-soluble materials, sugars, and electrolytes. Thus arranged, the surface of the filter may collect and eventually crystallize some of the salts and sugars reducing the venting/permeability of the filter. By intermittently presenting (e.g., delivering) fresh dialysate solution to the filter using, for example, pulsating flow, the water-soluble salts and sugars collecting on the surface of the filter can be dissolved back into the dialysate solution. Alternatively, in cases where purified water is used to create the dialysate solution, purified water could be introduced into the air chamber 300, 300' via, for example, pulsating flow, to rinse the filter free of salts and sugars.

The system described herein has been explained in connection with the dialysis machine 200 having a particular configuration. It is contemplated that the system described herein may be used with dialysis machines having other configurations, for example, different types of dialysis machines and/or dialysis machines having cassettes positionable in other configurations and having other features, such as different types of pumps and/or dialysate heating systems, such an in-line dialysate heating systems. The system described herein may be used with any appropriate dialysis machine and/or other medical devices utilizing disposable cassettes that would benefit from air management in the cassette. For example, for a description of another type of dialysis machine with which the system described herein may be incorporated, references is made to US 2019/0076590 A1 to Plahey et al., cited above and incorporated herein by reference.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A dialysis system, comprising:
a dialysis machine including a cavity;
a disposable cassette positionable within the cavity, the disposable cassette being in fluid communication with a patient and a dialysate bag;
an air chamber including an air vent coupled to the disposable cassette, the air chamber and the air vent being arranged and configured to allow air content to move out of the air chamber through the air vent;
an air filter configured to allow the air content to move through the air vent;
one or more pressure sensors configured to detect a pressure spike in the air chamber, the pressure spike based on a pressure limit of the air filter, and the pressure spike resulting from the air content being removed from the air chamber; and
at least one pump configured to pressurize the air chamber to push the air content out of the air chamber and through the air filter and the air vent up to a point where the pressure spike is detected via the one or more pressure sensors;
wherein the air content is moved into the air chamber via a negative pressure from a siphoning effect caused by fluid flow from a drain line in fluid communication with the air chamber, the negative pressure in the air chamber pulling the air content from the disposable cassette into the air chamber and to drain.

2. The dialysis system of claim 1, wherein the disposable cassette is arranged and configured so that, in use, the air content in the dialysate is directed into the air chamber and through the air vent.

3. The dialysis system of claim 1, wherein the air chamber is integrally formed with the disposable cassette.

4. The dialysis system of claim 3, wherein the air chamber is formed in a top portion of the disposable cassette.

5. The dialysis system of claim 3, the machine being arranged and configured so that the air content in the dialysate is detectable via the one or more pressure sensors, and when the air content in the dialysate exceeds a target value, the one or more valves are controllable to direct the air content into the air chamber.

6. The dialysis system of claim 1, wherein the air chamber is pressurized to move the air content out of the air chamber.

7. The dialysis system of claim 1, wherein the air filter is a hydrophobic filter.

8. The dialysis system of claim 1, wherein the air chamber is formed in a separate housing, the air chamber being in fluid communication with the disposable cassette.

9. The dialysis system of claim 8, wherein the air chamber is coupled to the disposable cassette via a membrane.

10. The dialysis system of claim 8, wherein the air chamber is coupled to the disposable cassette via a one-way valve.

11. A disposable cassette being in fluid communication with a patient and a dialysate bag for transferring dialysate therebetween, the disposable cassette comprising:

an air chamber including an air vent, the air chamber and the air vent being arranged and configured to allow air content to move out of the air chamber through the air vent;

an air filter configured to allow the air content to move through the air vent;

one or more pressure sensors configured to detect a pressure spike in the air chamber, the pressure spike based on a pressure limit of the air filter and resulting from the air content being removed from the air chamber; and at least one pump configured to pressurize the air chamber to move the air content out of the air chamber and through the air filter and the air vent until the pressure spike is detected via the one or more pressure sensors;

wherein the air content is moved into the air chamber via a negative pressure from a siphoning effect caused by fluid flow from a drain line in fluid communication with the air chamber, the negative pressure in the air chamber pulling the air content from the disposable cassette into the air chamber and to drain.

12. The disposable cassette of claim 11, further comprising:

one or more valves for directing the air content into the air chamber when the air content in the dialysate exceeds a target value detected by the one or more pressure sensors.

13. The disposable cassette of claim 11, wherein the air chamber is integrally formed with the disposable cassette.

14. The disposable cassette of claim 13, wherein the air chamber is formed in a top portion of the disposable cassette.

15. The disposable cassette of claim 11, wherein the air chamber is pressurized to move the air content out of the air chamber.

16. The disposable cassette of claim 11, wherein the air chamber is formed in a separate housing, the air chamber being in fluid communication with the disposable cassette.

17. The disposable cassette of claim 16, wherein the air chamber is coupled to the disposable cassette via a membrane or a one-way valve.

18. The dialysis system of claim 1, wherein the pressure of the air chamber is regulated within the pressure limit and to facilitate movement of the air content through the air vent.

19. The disposable cassette of claim 11, wherein the pressure of the air chamber is regulated within the pressure limit and to facilitate movement of the air content through the air vent.

* * * * *